US00PP37203P2

(12) United States Plant Patent
van Dijk

(10) Patent No.: US PP37,203 P2
(45) Date of Patent: Jan. 6, 2026

(54) ***ANTHURIUM* PLANT NAMED 'AN2828318'**

(50) Latin Name: *Anthurium andreanum*
Varietal Denomination: AN2828318

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/791,406

(22) Filed: Jul. 31, 2024

(51) Int. Cl.
*A01H 5/02* (2018.01)
*A01H 6/10* (2018.01)

(52) U.S. Cl.
USPC ..... Plt./369

(58) Field of Classification Search
USPC ..... Plt./365, 369
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Anthurium* plant named 'AN2828318', characterized by its compact, upright to outwardly arching and uniform plant habit; freely clumping growth habit; bushy and dense plants; narrowly cordate dark green-colored leaves; freely flowering habit; inflorescences that are positioned within to slightly above the foliar plane on strong and mostly upright scapes; broadly cordate red-colored spathes and darker red-colored spadices.

2 Drawing Sheets

Figure 1:
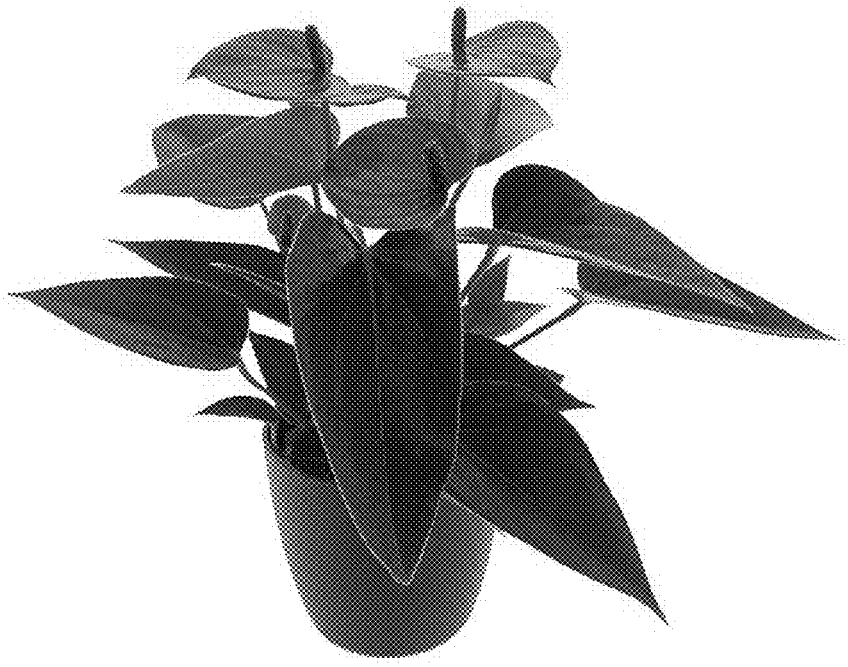

Botanical designation: *Anthurium andreanum.*
Cultivar denomination: 'AN2828318'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Nov. 22, 2023, application number 2023/2441. Foreign priority is not claimed to this application.

BACKGROUND OF THE INVENTION

The present invention relates to a new and distinct cultivar of *Anthurium* plant, botanically known as *Anthurium andreanum* and hereinafter referred to by the name 'AN2828318'.

The new *Anthurium* plant is a product of a controlled breeding program conducted by the Inventor in Bleiswijk, The Netherlands. The objective of the breeding program is to create new relatively compact and freely-clumping *Anthurium* plants with attractive and durable red-colored spathes.

The new *Anthurium* plant originated from a cross-pollination made by the Inventor in September 2015 in Bleiswijk, The Netherlands of a proprietary selection of *Anthurium andreanum* identified as code number 12-028038-0001, not patented, as the female, or seed, parent with *Anthurium andreanum* 'Anthdatam', disclosed in U.S. Plant Pat. No. 27,699, as the male, or pollen, parent. The new *Anthurium* was discovered and selected by the Inventor as a single flowering plant within the progeny of the stated cross-pollination in a controlled greenhouse environment in Bleiswijk, The Netherlands in May 2017.

Asexual reproduction of the new *Anthurium* plant by in vitro meristem propagation in a controlled environment in Bleiswijk, The Netherlands since July, 2019 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2828318'. These characteristics in combination distinguish 'AN2828318' as a new and distinct *Anthurium* plant:

1. Compact, upright to outwardly arching and uniform plant habit.
2. Freely clumping growth habit; bushy and dense plants.
3. Narrowly cordate dark green-colored leaves.
4. Freely flowering habit.
5. Inflorescences that are positioned within to slightly above the foliar plane on strong and mostly upright scapes.
6. Broadly cordate red-colored spathes and darker red-colored spadices.

Plants of the new *Anthurium* differ primarily from plants of the female parent selection in the following characteristics:

1. Spathes of plants of the new *Anthurium* are red in color whereas spathes of plants of the female parent selection are white in color.
2. Spadices of plants of the new *Anthurium* are dark red in color whereas spadices of plants of the female parent selection are creamy white and yellow in color.

Plants of the new *Anthurium* differ primarily from plants of the male parent, 'Anthdatam', in the following characteristics:

1. Plants of the new *Anthurium* are more freely clumping than plants of 'Anthdatam'.
2. Spathes of plants of the new *Anthurium* are not as broad as spathes of plants of 'Anthdatam'.
3. Spathes of plants of the new *Anthurium* are red in color whereas spathes of plants of 'Anthdatam' are pink in color.
4. Spadices of plants of the new *Anthurium* are dark red in color whereas spadices of plants of 'Anthdatam' are red purple and orange in color.

Plants of the new *Anthurium* can also be compared to plants of *Anthurium andreanum* 'Anthdinwaq', disclosed in U.S. Plant Pat. No. 26,048. In side-by-side comparisons, plants of the new *Anthurium* differ primarily from plants of 'Anthdinwaq' in the following characteristics:

1. Inflorescences of plants of the new *Anthurium* are held within to slightly above the foliar plane whereas inflorescences of plants of 'Anthdinwaq' are held way above the foliar plane.
2. Spathes of plants of the new *Anthurium* are red in color whereas spathes of plants of 'Anthdinwaq' are pink in color.
3. Spadices of plants of the new *Anthurium* are not as tapering as spadices of plants of 'Anthdinwaq'.
4. Spadices of plants of the new *Anthurium* are dark red in color whereas spadices of plants of 'Anthdinwaq' are light purple in color.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2828318' grown in a container.

Figure 2:
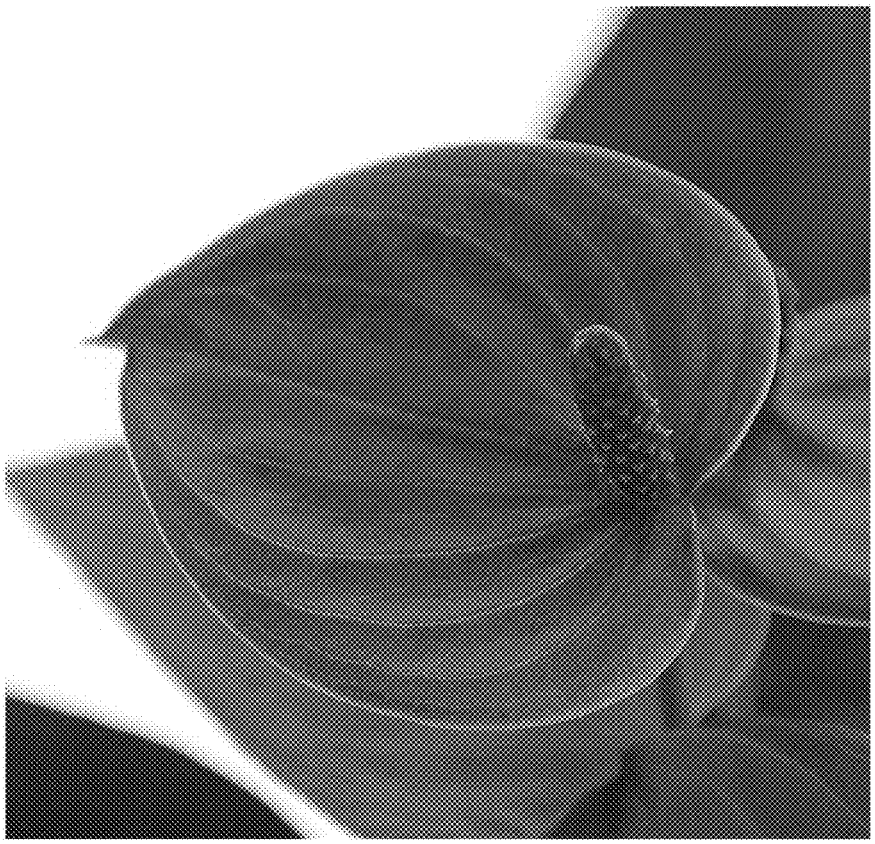

The photograph on the second sheet (FIG. 2) is a close-up view of a typical inflorescence of 'AN2828318'.

DETAILED BOTANICAL DESCRIPTION

The aforementioned photographs and following observations and measurements describe plants grown in 9-cm containers during the late winter in a glass-covered greenhouse in Bleiswijk, The Netherlands. Plants were grown under conditions and practices which approximate those generally used in commercial *Anthurium* production. During the production of the plants, day and night temperatures ranged from about 19° C. to 22.5° C. and light levels ranged from 100 μmol to 200 μmol. Plants were nine months old when the photographs and the detailed description were taken. In the following description, color references are made to The Royal Horticultural Society Colour Chart, 2015 Edition, except where general terms of ordinary dictionary significance are used.

Botanical classification:*Anthurium andreanum* 'AN2828318'.

Parentage:

*Female, or seed, parent.*—Proprietary selection of *Anthurium andreanum* identified as code number 12-028038-0001, not patented.

*Male, or pollen, parent.*—*Anthurium andreanum* 'Anthdatam', disclosed in U.S. Plant Pat. No. 27,699.

Propagation:

*Type.*—By in vitro meristem propagation.

*Time to initiate roots, summer and winter.*—About two weeks at temperatures about 19° C. to 22.5° C.

*Time to produce a rooted young plant, summer and winter.*—About six to eight weeks at temperatures about 19° C. to 22.5° C.

*Root description.*—Medium in thickness, fibrous; typically creamy white slightly tinged with pink in color, actual color of the roots is dependent on substrate composition, water quality, fertilizer type and formulation, substrate temperature and physiological age of roots.

*Rooting habit.*—Freely branching, medium density.

Plant description:

*Plant shape.*—Compact, upright to outwardly spreading and uniform plant habit; overall shape, roughly broadly obovate to close to spherical.

*Growth habit.*—Freely clumping habit with about six clumps developing per plant imparting a bushy and dense appearance.

*Plant height, from soil level to top of leaf plane.*—About 15.3 cm.

*Plant height, from soil level to top of inflorescences.*—About 20.2 cm.

*Plant diameter or spread.*—About 31.1 cm.

Leaf description:

*Arrangement.*—Alternate; simple; about three leaves per clump.

*Length.*—About 11.6 cm.

*Width.*—About 7.2 cm.

*Shape.*—Narrowly cordate.

*Apex.*—Apiculate with a short mucronate tip.

*Base.*—Cordate to truncate; basal lobes free.

*Margin.*—Entire; flat to slightly and coarsely undulate.

*Texture and luster, upper and lower surfaces.*—Smooth, glabrous; coriaceous; glossy.

*Venation pattern.*—Pinnate.

*Color.*—Developing leaves, upper surface: Close to 143A. Developing leaves, lower surface: Close to 144A. Fully expanded leaves, upper surface: Close to a blend of NN137A and 139A; narrow marginal edges, close to 144A; venation, close to 144A. Fully expanded leaves, lower surface: Close to a blend of 144A and 146B; venation, close to N144C.

*Petioles.*—Length: About 11.3 cm. Diameter: Distally, about 2.5 mm; proximally, about 4 mm. Texture and luster, upper and lower surfaces: Smooth, glabrous; slightly glossy. Color, upper surface: Close to a blend of 144A and 144B. Color, lower surface: Close to 144B. Geniculum length: About 1.5 cm. Geniculum diameter: About 3 mm by 3.5 mm. Geniculum texture, upper and lower surfaces: Smooth, glabrous. Geniculum color, upper surface: Close to 144A. Geniculum color, lower surface: Close to 146D. Wing length: About 1.8 cm. Wing diameter: About 4 mm. Wing color: Close to 144A; towards the margins, close to 144C.

Inflorescence description:

*Inflorescence arrangement and flowering habit.*—Spathes with spadices held within and slightly above the foliar plane on erect scapes; flowering structures arise from leaf axils; freely and continuous flowering year-round in controlled temperature greenhouses in The Netherlands; typically about seven developing and developed inflorescences per plant at one time; inflorescence development commences about 2.5 to 3.5 months after planting.

*Inflorescence longevity*.—Depending on temperature, spathes maintain good substance for about two months on the plant; inflorescences persistent.

*Fragrance*.—None detected.

*Spathes*.—Length: About 5.7 cm. Width: About 5.5 cm. Shape: Broadly cordate; typically flat to slightly concave. Apex: Abruptly and broadly acute with a mucronate tip. Base: Cordate to truncate. Margin: Entire; flat to slightly and coarsely undulate. Aspect: About 80° from the scape axis. Texture and luster, upper and lower surfaces: Smooth, glabrous; moderately leathery; slightly rugose; glossy. Color: When developing, front surface: Close to 46C; at the apex, close to 145C. When developing, rear surface: Close to 52B; at the apex, close to 145C; towards the base, close to 52A. Fully developed, front surface: Close to a blend of N45C and 46B; at the apex, close to 145C to 145D; towards the base, slightly tinged with close to 146A; with subsequent development, close to a blend of N45C and 46C, at the apex, close to 145B and 145C, towards the base, close to 144A and 144B with basal venation, close to 200A and 200B. Fully developed, rear surface: Close to 52B; at the apex, close to 145C to 145D; towards the base, tinged with close to 145B; venation, close to 182A; with subsequent development, color becoming closer to 52B and 53D, at the apex, close to 150C and 150D, towards the base, tinged with close to 146D and venation, close to 147A and 147B.

*Spadices*.—Length: About 1.9 cm. Diameter: About 5.5 mm. Shape: Columnar, slightly tapering towards the apex; apex, obtuse; base, obtuse; in cross-section, rounded. Aspect: About 77.5° from the spathe axis and about 2.5° from the scape axis. Color: Immature: Close to 46A; towards the apex, close to 46B and 46C. Mature: Close to 60A. Flowers: Type: Hermaphroditic. Quantity per spadix: Numerous, about 90. Height: Less than 0.5 mm. Diameter: About 2 mm. Shape: Roughly square. Anther color: Close to 60A. Pollen color: Close to 155D. Stigma color: Close to 185A.

*Scapes*.—Length: About 15.4 cm. Diameter: About 3 mm. Aspect: About 20° from vertical. Color: Close to 144A.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures about 30° C. and to be hardy to USDA Hardiness Zone 10.

It is claimed:

1. A new and distinct *Anthurium* plant named 'AN2828318' as herein illustrated and described.

* * * * *